(12) United States Patent
Raphael et al.

(10) Patent No.: US 10,345,287 B2
(45) Date of Patent: Jul. 9, 2019

(54) CALIBRATING SINGLE PLASMONIC NANOSTRUCTURES FOR QUANTITATIVE BIOSENING

(71) Applicants: Marc P. Raphael, Washington, DC (US); Joseph A. Christodoulides, Alexandria, VA (US); Jeff M. Byers, Fairfax Station, VA (US)

(72) Inventors: Marc P. Raphael, Washington, DC (US); Joseph A. Christodoulides, Alexandria, VA (US); Jeff M. Byers, Fairfax Station, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 572 days.

(21) Appl. No.: 14/039,326

(22) Filed: Sep. 27, 2013

(65) Prior Publication Data
US 2014/0095100 A1 Apr. 3, 2014

Related U.S. Application Data

(60) Provisional application No. 61/839,428, filed on Jun. 26, 2013, provisional application No. 61/706,867, filed on Sep. 28, 2012.

(51) Int. Cl.
*G01N 21/27* (2006.01)
*G01N 21/552* (2014.01)
(Continued)

(52) U.S. Cl.
CPC ......... *G01N 33/483* (2013.01); *B82Y 15/00* (2013.01); *G01N 21/276* (2013.01); *G01N 21/554* (2013.01)

(58) Field of Classification Search
None
See application file for complete search history.

(56) References Cited

U.S. PATENT DOCUMENTS

| 7,291,284 B2 * | 11/2007 | Mirkin ................. B82Y 10/00 216/41 |
| 2002/0058273 A1 * | 5/2002 | Shipwash ............ B01L 3/5027 435/6.12 |

(Continued)

OTHER PUBLICATIONS

A New Methodology for Quantitative LSPR Biosensing and Imaging.*

(Continued)

*Primary Examiner* — Gregory J Toatley, Jr.
*Assistant Examiner* — Brandon J Becker
(74) *Attorney, Agent, or Firm* — US Naval Research Laboratory; Rebecca L. Forman (57) ABSTRACT

A method for calibrating multiple nanostructures in parallel for quantitative biosensing using a chip for localized surface plasmon resonance (LSPR) biosensing and imaging. The chip is a glass coverslip compatible for use in a standard microscope with at least one array of functionalized plasmonic nanostructures patterned onto it using electron beam nanolithography. The chip is used to collect CCD-based LSPR imagery data of each individual nanostructure and LSPR spectral data of the array. The spectral data is used to determine the fractional occupancy of the array. The imagery data is modeled as a function of fractional occupancy to determine the fractional occupancy of each individual nanostructure.

7 Claims, 5 Drawing Sheets

(51) Int. Cl.
*G01N 33/483* (2006.01)
*B82Y 15/00* (2011.01)

(56) References Cited

U.S. PATENT DOCUMENTS

| | | | | |
|---|---|---|---|---|
| 2002/0100164 | A1* | 8/2002 | Tanaka | G03F 1/56 29/832 |
| 2002/0119579 | A1* | 8/2002 | Wagner | B82Y 5/00 436/518 |
| 2004/0248144 | A1* | 12/2004 | Mir | C12Q 1/6818 435/6.11 |
| 2005/0063982 | A1* | 3/2005 | Argon | A01K 67/0276 424/185.1 |
| 2007/0224240 | A1* | 9/2007 | Toner | A61L 31/16 424/423 |
| 2007/0224617 | A1* | 9/2007 | Quake | G01N 33/5302 435/6.12 |
| 2009/0111709 | A1* | 4/2009 | Burke | C40B 30/04 506/9 |
| 2009/0208081 | A1* | 8/2009 | Saha | G16H 50/70 382/131 |
| 2010/0291566 | A1* | 11/2010 | Daunert | G01N 33/6893 435/6.16 |
| 2014/0093977 | A1 | 4/2014 | Raphael et al. | |

OTHER PUBLICATIONS

Plasmon-Enhanced Colorimetric ELISA with Single Molecule Sensitivity.*

Raphael et al., "A New Methodology for Quantitative LSPR Biosensing and Imaging," Anal. Chem., 84 (3), 1367-1373 (2012).

Chen et al., "Plasmon-Enhanced Colorimetric ELISA with Single Molecule Sensitivity," Nano Lett. 11 (4), 1826-1830 (2011).

Dahlin et al., "Improving the Instrumental Resolution of Sensors Based on Localized Surface Plasmon Resonance," Anal. Chem., 2006, 78, 4416-4423.

Haes et al., "A Nanoscale Optical Biosensor: Sensitivity and Selectivity of an Approach Based on the Localized Surface Plasmon Resonance Spectroscopy of Triangular Silver Nanoparticles," J. Am. Chem. Soc., 2002, 124, 10596-10604.

Haes et al., "A unified view of propagating and localized surface plasmon resonance biosensors," Anal. Bioanal. Chem., 2004, 379, 920-930.

Nath et al., "A Colorimetric Gold Nanoparticle Sensor to Interrogate Biomolecular Interactions in Real Time on a Surface," Anal. Chem., 2002, 74, 504-509.

Riboh et al., "A Nanoscale Optical Biosensor: Real-Time Immunoassay in Physiological Buffer Enabled by Improved Nanoparticle Adhesion," J. Phys. Chem. B, 2003, 107, 1772-1780.

Englebienne, "Use of colloidal gold surface plasmon resonance peak shift to infer affinity constants from the interactions between protein antigens and antibodies specific for single or multiple epitopes," Analyst, 1998, 123, 1599-1603.

Dahlin et al., "Specific Self-Assembly of Single Lipid Vesicles in Nanoplasmonic Apertures in Gold," Adv. Mater., 2008, 20, 1436-1442.

Haes et al., "A Localized Surface Plasmon Resonance Biosensor: First Steps toward an Assay for Alzheimer's Disease," Nano Lett., 2004, 4, 6, 1029-1034.

Haes et al., "Nanoscale plasmonics begins to unravel Alzheimer's disease," Laser Focus World, 2005, 41, 6, 105.

Feng et al., "Nanoscale Plasmonic Interferometers for Multispectral, High-Throughput Biochemical Sensing," Nano Lett., 2012, 12, 602-609.

Endo et al., "Label-free cell-based assay using localized surface plasmon resonance biosensor," Analytica Chimica Acta, 2008, 614, 182-189.

Hall et al., "A Conformation- and Ion-Sensitive Plasmonic Biosensor," Nano Lett. 2011, 11, 1098-1105.

Abbas et al., "New trends in instrumental design for surface plasmon resonance-based biosensors," Biosensors and Bioelectronics, 2011, 26, 1815-1824.

Haes et al., "Plasmonic Materials for Surface-Enhanced Sensing and Spectroscopy," MRS Bulletin, 2005, 30, 368-375.

Zhao et al., "Localized surface plasmon resonance biosensors," Nanomedicine, 2006, 1, 2, 219-228.

Yu et al., "Quantitative Evaluation of Sensitivity and Selectivity of Multiplex NanoSPR Biosensor Assays," Biophysical Journal, 2007, 93,3684-3692.

Lindquist et al., "Sub-micron resolution surface plasmon resonance imaging enabled by nanohole arrays with surrounding Bragg mirrors for enhanced sensitivity and isolation," Lab Chip, 2009, 9, 382-387.

Huang et al., "Micro- and Nanotechnologies for Study of Cell Secretion," Anal. Chem., 2011, 83, 4393-4406.

Kita et al., "Microelectrodes for studying neurobiology," Chemical Biology, 2008, 12, 491-496.

Gujral et al., "Emerging Miniatruized Proteomic Technologies to Study Cell Signaling in Clinical Samples," Science Signaling, 2009, 2, 93, 1-4.

Mayer et al., "A single molecule immunoassay by localized surface plasmon resonance," Nanotechnology, 2010, 21, 255503.

Nusz et al. "Label-Free Plasmonic Detection of Biomolecular Binding by a Single Gold Nanorod," Anal. Chem., 2008, 80, 984-989.

Hinrichsen et al., "Geometry of Random Sequential Adsorption," Journal of Statistical Physics, 1986, 44, 5/6, 793-827.

Jung et al., "Binding and Dissociation Kinetics of Wild-Type and Mutant Streptavidins on Mixed Biotin-Containing Alkylthiolate Monolayers," Langmuir, 2000, 16, 9421-9432.

* cited by examiner

CALIBRATING SINGLE PLASMONIC NANOSTRUCTURES FOR QUANTITATIVE BIOSENING

PRIORITY CLAIM

This Application claims priority from U.S. Provisional Application No. 61/706,867 filed on Sep. 28, 2012 by Marc P. Raphael et al., entitled "CALIBRATING SINGLE PLASMONIC NANOSTRUCTURES FOR QUANTITATIVE BIOSENSING" and U.S. Provisional Application No. 61/839,428 filed on Jun. 26, 2013 by Marc P. Raphael et al., entitled "SILICON BACKING RING AND MULTIPLEXING APPLICATIONS FOR LSPR IMAGING." The entire contents of each provisional application and all references cited throughout this application and the provisional applications are incorporated herein by reference.

CROSS REFERENCE

Cross reference is made to copending application Ser. No. 14/039,288, filed contemporaneously herewith, entitled "LIGHT MICROSCOPY CHIPS AND DATA ANALYSIS METHODOLOGY FOR QUANTITATIVE LOCALZIED SURFACE PLASMON RESONANCE (LSPR) BIOSENSING AND IMAGING," by Marc P. Raphael, et al. the disclosure of which is incorporated herein by reference in its entirety.

BACKGROUND OF THE INVENTION

Field of the Invention

The present invention relates to localized surface plasmon resonance (LSPR) imaging and quantitative biosensing.

Description of the Prior Art

The utilization of the localized surface plasmon resonance (LSPR) observed in metallic nanostructures for label-free biosensing is relatively recent but its applicability has already proven to be far reaching. Early studies were primarily proof-of-principle, demonstrating techniques which had the sensitivity to detect the binding of well-characterized receptor ligand pairs such as streptavidin and biotin. (A. B. Dahlin et al., *Anal. Chem.*, 78, (13), 4416-4423 (2006); A. J. Haes et al., *J. Am. Chem. Soc.*, 124, (35), 10596-10604 (2002); A. J. Haes et al., *Analytical and Bioanalytical Chemistry*, 379, (7-8), 920-930 (2004); N. Nath et al., *Anal. Chem.*, 74, (3), 504-509 (2002); J. C. Riboh et al., *J. Phys. Chem. B*, 107, (3), 1772-1780 (2003); and P. Englebienne, *Analyst*, 123, (7), 1599-1603 (1998)). More applied studies followed, such as the detection of liposomes and Alzheimer's-related antibodies. (A. B. Dahlin et al., *Adv. Mat.*, 20 (8), 1436-+ (2008); A. J. Haes et al., *Nano Letters*, 4, (6), 1029-1034 (2004); A. J. Haes et al., *Laser Focus World*, 41, (6), 105-+ (2005)). The applications have grown in sophistication such that LSPR has now been applied to plasma-enhanced ELISA (S. Chen et al., *Nano Letters*, 11, (4), 1826-1830 (2011)), interferometry-based biosensing (J. Feng et al. et al., *Nano Letters*, 12, (2), 602-609 (2012), cell-based assays (T. Endo et al., *Analytica Chimica Acta*, 614, (2), 182-189 (2008), and the measurement of protein conformational changes (W. P. Hall et al., *Nano Letters*, 11, (3), 1098-1105 (2011)) to name a few. (A. Abbas et al., *Biosens. Bioelectron.*, 26, (5), 1815-1824 (2011); A. J. Haes et al., *MRS Bulletin*, 30, (5), 368-375 (2005); J. Zhao et al., *Nanomedicine*, 1, (2), 219-228 (2006); (C. Yu et al., "Quantitative evaluation of sensitivity and selectivity of multiplex nanoSPR biosensor assays," *Biophys. J.*, 93, (10), 3684-92).

Advances in instrumentation and analysis now allow for many of these measurements to be made on individual nanostructures, opening the door for imaging applications in which hundreds or thousands of nanostructures are measured in parallel. (S. Chen et al., *Nano Letters*, 11, (4), 1826-1830 (2011); M. P. Raphael et al., *Anal. Chem.*, 84, (3), 1367-1373 (2012); N. C. Lindquist et al., *Lab on a Chip*, 9, (3), 382-387 (2009)). As such, LSPR imaging has the potential to take advantage of each sensor's nanoscale dimensions to map complex spatio-temporal variations in analyte concentration, such as those encountered in live-cell applications (Y. X. Huang et al., *Anal. Chem.*, 83, (12), 4394-4406 (2011) and J. M. Kita et al., *Current Opinion in Chemical Biology*, 12, (5), 491-496 (2008)), and to enable highly-compact and multiplexed proteomic arrays requiring only microliter sample volumes. (T. S. Gujral et al., *Sci. Signal*, 2, (94) (2009)). Because the measurements are label-free, LSPR imaging avoids the time consuming task of labeling the analyte and eliminates fluorescence-based complications such as photobleaching and quenching.

A roadblock to the realization of these applications is that each nanostructure must be individually calibrated so that its response to analyte can be quantitatively analyzed. That is to say, the single nanostructure must go beyond being a detector of analyte, which is the current norm, to the point where it can be used as an instrument for the quantification of important biochemical parameters such as kinetic rate constants and analyte concentration. The sequential calibration of hundreds or thousands of individual nanostructures, however, is time consuming and impractical. Thus, the calibration must take place in an imaging, or batch mode, which allows for simultaneous data collection and analysis on a collection of nanostructures. For quantitative analysis, a key parameter to be determined for each nanostructure is the time-dependent fractional occupancy of surface-bound receptors, $f(t)$. Once known, fits to $f(t)$ can be used to determine kinetic rate constants if the concentration of analyte is known or, conversely, for determining concentration if the rate constants are known.

BRIEF SUMMARY OF THE INVENTION

The present invention provides a method for calibrating multiple nanostructures in parallel for quantitative biosensing using a chip for localized surface plasmon resonance (LSPR) biosensing and imaging. The chip is a glass coverslip compatible for use in a standard microscope with at least one array of functionalized plasmonic nanostructures patterned onto it using electron beam nanolithography. The chip is used to collect CCD-based LSPR imagery data of each individual nanostructure and LSPR spectral data of the array. The spectral data is used to determine the fractional occupancy of the array. The imagery data is modeled as a function of fractional occupancy to determine the fractional occupancy of each individual nanostructure. This calibration allows for the mapping of the fractional occupancy of surface-bound receptors at individual nanostructures with nanomolar sensitivity and a temporal resolution of 225 ms.

Some features and advantages of this invention include:
  The fabrication of the arrays by electron-beam lithography enables the production of highly uniform nanostructures, as confirmed by both size and spectral characterizations.

Hundreds of individual nanostructures can be calibrated in parallel.

It is integrated into a standard wide field microscopy setup that incorporates a number of other imaging techniques, such as fluorescence, differential interference contrast, and brightfield imaging.

The imaging mode of the LSPR microscope allows for spatial resolutions limited only by the size of the nanostructures.

The temporal resolution of the imaging mode is in the hundreds of milliseconds allowing for fast bio-kinetic processes to be measured.

Complex environments can be monitored without sensor biofouling, such as those encountered in live cell microscopy.

These and other features and advantages of the invention, as well as the invention itself, will become better understood by reference to the following detailed description, appended claims, and accompanying drawings.

BRIEF DESCRIPTION OF THE DRAWINGS

FIG. 2(a) shows mean intensity for the entire array (square light gray ROI, 84×84 pixels). FIG. 2(b) shows mean intensity of a single nanostructure (square black ROI, 4×4 pixels). FIG. 2(c) shows a comparison of the normalized responses of the whole array and the single nanostructure. Also plotted in FIGS. 2(a) and (b) are the results of a drift study that preceded the introduction of analyte (black squares). The inset images in FIGS. 2(a) and (b) show a contrast-enhanced CCD image of the array that highlights the variations in nanostructure intensities. All studies were conducted in serum-free medium at a flow rate of 10 µL/min.

FIG. 4(a) shows an error estimate map of $\sigma_i$ for the anti-c-myc harvested antibody study, as calculated by a 4×4 pixel (410×410 nm) sliding ROI window, plotted for deviations between $f_I$ and $f_S$ ranging from 0 to 0.1. Four plots of select ROIs are shown in FIGS. 4(b)-(e) to illustrate the deviations associated with a given $\sigma_i$. The color of the ROI data points are matched with that of the ROI square label on the response map with (b) $\sigma_i$=0.03 (c) $\sigma_i$=0.05 (d) $\sigma_i$=0.10 and (e) $\sigma_i$=0.42. The vertical dashed line indicates when the 250 nM of commercial anti-c-myc was injected.

DETAILED DESCRIPTION OF THE INVENTION

The present invention provides a localized surface plasmon resonance (LSPR) imaging and analysis technique that enables the calibration of hundreds of individual gold nanostructures in parallel. The calibration enables the mapping of the fractional occupancy of surface-bound receptors at individual nanostructures with a temporal resolution of 225 ms. Some features of this invention are (1) the fabrication of the arrays by electron-beam lithography for the production of highly uniform nanostructures, as confirmed by both size and spectral characterizations (2) the simultaneous measurement of spectra and imagery and (3) the combination of the spectral and imagery data into an analysis formalism that enables the determination of the fractional occupancy of surface bound receptors at individual nanostructures, f(r, t), where r denotes the location on the substrate and t denotes time. In addition, the technique is fully compatible with fluorescence and DIC microscopy techniques and can be used in complex fluid environments like serum free medium without degradation of the sensors.

Using the present invention, the imagery of single nanostructures can encode the same information as the ensemble measurement of the entire array as measured spectroscopically. In other words, if the array is subjected to a uniform spatial distribution of analyte, the optical response of nanostructure-sized regions of interest (ROIs) can be calibrated to that of the ensemble fractional occupancy found by spectroscopy. It is not obvious that this should be possible since the image sums up all the spectral information and individual nanostructures can be subject to stochastic processes that average away when the entire array is used. Using an array of four hundred nanostructures, it was demonstrated that this technique allows for the qualitative detection of commercially available anti-c-myc antibodies with single nanostructure resolution using only a CCD camera. Using the same array of nanostructures, the calibration methodology that enables the quantification of the CCD-based measurements for the determination of f(r,t) is detailed. As a demonstration of this technique's applicability to molecular and cell biology, the calibrated array was used for quantitative LSPR imaging of anti-c-myc antibodies that were harvested from the hybridoma cell line 9E10 without the need for their further purification or processing. All experiments were conducted in the same serum free medium (SFM) used for cell culturing applications.

Fabrication and Functionalization of the Nanostructures

The nanostructures were fabricated on No. 1.5, 25.4 mm diameter borosilicate glass coverslips by electron-beam lithography (EBL). The structures were circular in cross section with a diameter 70±5 nm, 75±2 nm in height, and patterned into 20×20 arrays with a spacing of 400 nm. The chip was cleaned by plasma ashing in 5% hydrogen, 95% argon mixture and then functionalized by immersion in a two-component thiol solution (0.5 mM), consisting of a 3:1 ratio of SH—$(CH_2)_8$-$EG_3$-OH (SPO) to SH—$(CH_2)_{11}$-$EG_3$-$NH_2$ (SPN), for 18 hours (Prochimia, Poland). The SPN component of the SAM layer was first reacted with a 10 mg/mL solution of the heterobifunctional crosslinker sulfo-N-succinimidyl-4-formylbenzamide (Sulfo-S-4FB, Solulink) in 100 mM phosphate buffered saline (100 mM PBS, Thermo Scientific) and then conjugated to the c-myc peptide (HyNic-c-myc-tag, Solulink) according to the manufacturer's instructions. Anti-c-myc secreting hybridoma cells (MYC1-9E10.2, ATCC) were adapted to growth in serum-free medium containing 1% antibiotic/antimycotic by the sequential, stepwise reduction in fetal bovine serum content over a one-month culture period. The secretion of the 9E10.2 monoclonal antibodies (anti-c-myc) was confirmed and quantified by enzyme-linked immunosorbent assay (ELISA) using a BSA-c-myc peptide conjugate (~7 c-myc peptides per BSA) as the immobilized antigen (coated overnight at 5 µg/mL in 100 mM PBS at 4° C.). The details of the nanostructure fabrication by EBL, plasma ashing procedure and application of the SAM layer are described in M. P. Raphael et al., "A New Methodology for Quantitative LSPR Biosensing and Imaging," Anal. Chem., 84(3), 1367-73 (2012).

Optical Setup

CCD-based LSPR imaging, as well as LSPR spectra, were collected in a reflected light geometry with an inverted microscope (Zeiss Axio Observer) using Koehler illumination, a 63×, 1.4 numerical aperture (NA) oil-immersion objective and crossed-polarizers to reduce the background contribution from substrate-scattered light. Imagery and spectra were obtained simultaneously by placing a beam splitter at the output port of the microscope (FIG. 1a) and a long-pass filter with a 593 nm cut-off wavelength was placed before the CCD camera. For the spectral measurements, the focused image of the entire nanostructure array was projected on to the end of a 600 µm diameter optical fiber and the spectra were subsequently measured with a thermoelectrically-cooled, CCD-based spectrophotometer (Ocean Optics QE65000). The spectrophotometer integration time was 4 seconds. For image acquisition, the focused image of the array was projected on to a thermoelectrically-cooled CCD camera with 6.45×6.45 µm sized pixels (Hamamatsu ORCA $R^2$) and a frame integration time of 225 ms. Details of how the above setup was optimized for high contrast imaging of the gold nanostructures are described in M. P. Raphael et al., "A New Methodology for Quantitative LSPR Biosensing and Imaging," Anal. Chem., 84(3), 1367-73 (2012). Analyte was introduced under continuous flow conditions using a custom-made microfluidic cell at a flow rate of 10 µL/min. The microscope stage was equipped with a temperature controlled insert which kept the stage temperature and optical light train at 28.0±0.04° C. (PeCon GmbH). Under these conditions, the drifts in the x, y and z directions were less than 3 nm/min. For data analysis, all frames were aligned in x and y using a commercially available image-processing alignment algorithm (Zeiss Axiovision).

Qualitative Biosensing with Single Nanostructures

Figure 1A:
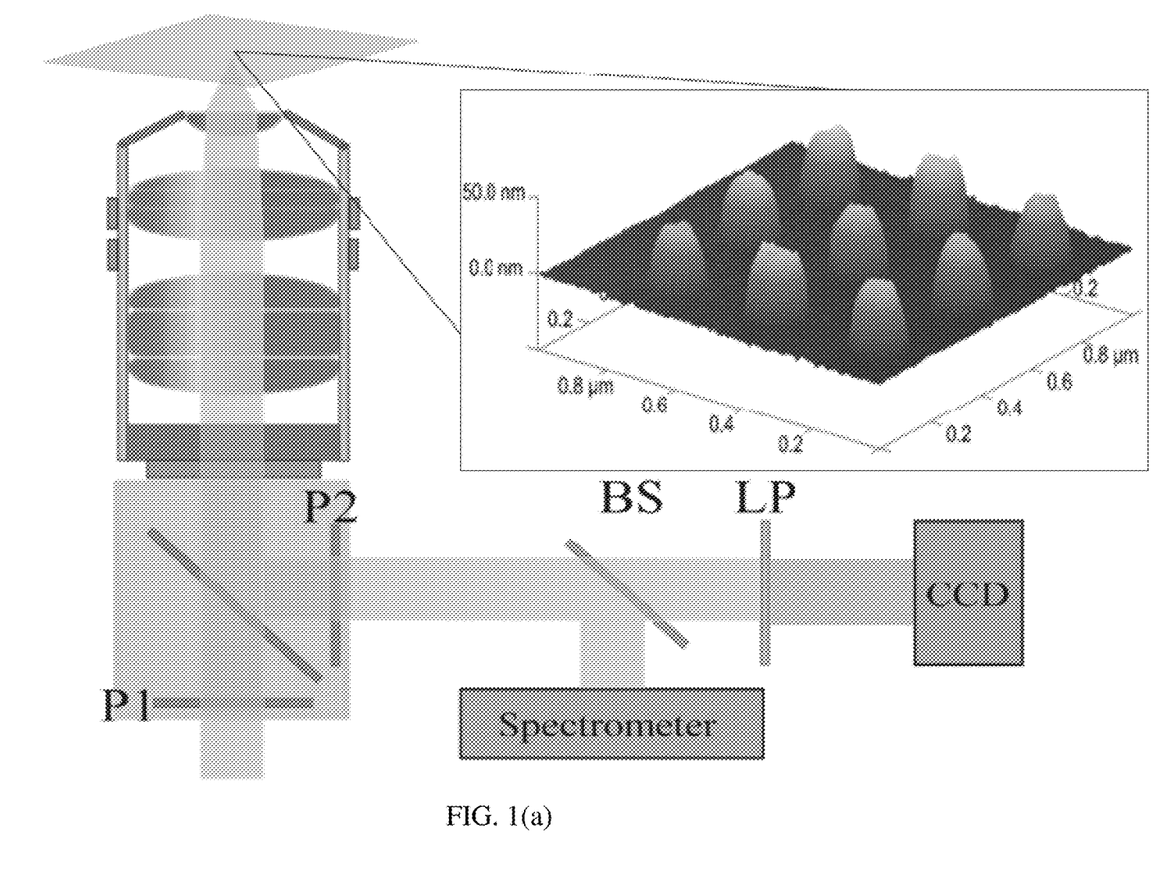
FIG. 1(a) is a diagram of the imaging and spectroscopy setup in which P1 and P2 are crossed polarizers, BS is a 50/50 beam splitter and LP is a long pass filter with a 593 nm cutoff. The inset shows an AFM scan of a witness array fabricated on the same chip.
Figure 1B:
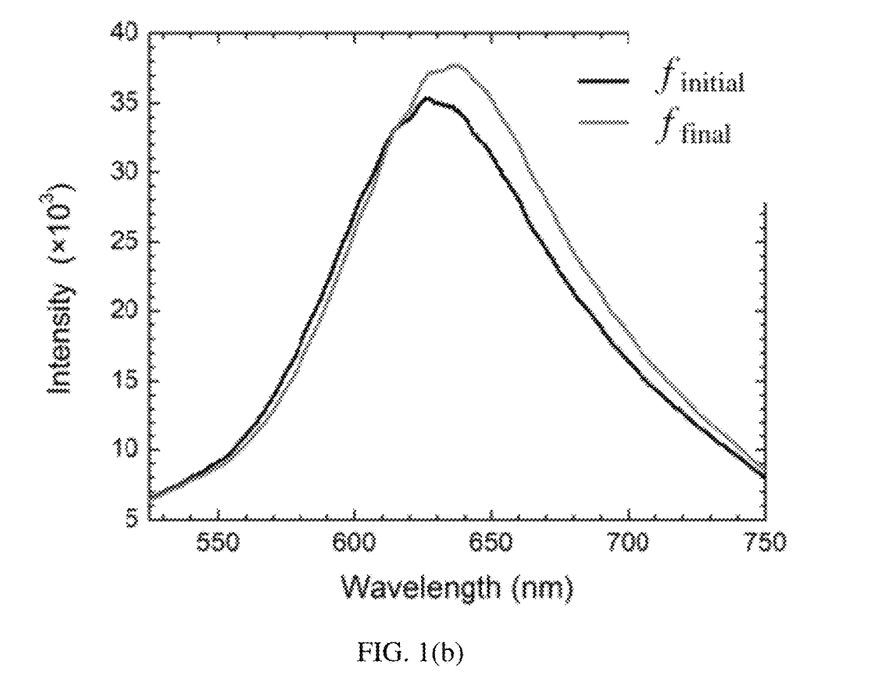
FIG. 1(b) shows two spectra from a specific-binding study in which 200 nM of anti-c-myc was introduced over the c-myc functionalized array (10 µL/min). The $f_{initial}$ spectrum (black) was taken before the anti-c-myc was introduced and the $f_{final}$ spectrum (gray) after one hour of exposure.

The imagery as well as LSPR spectra were simultaneously acquired by passing the reflected light through a 50/50 beam splitter (BS) as shown in FIG. 1(a). FIG. 1(b) shows two spectra from a specific-binding study in which 200 nM of anti-c-myc was introduced over a c-myc functionalized array at a flow rate of 10 µL/min. The $f_{initial}$ spectrum (black) was taken before the anti-c-myc was introduced and the $f_{final}$ spectrum (gray) was taken after one hour of exposure. The characteristic gray-shift of the peak position and the corresponding increase in counts from 605 nm to 750 nm are indicative of a local change in the dielectric constant of the medium caused by the specific binding of the anti-c-myc antibody. (A. B. Dahlin et al., "Improving the instrumental resolution of sensors based on localized surface plasmon resonance," Anal. Chem., 78, (13), 4416-23 (2006) and W. P. Hall et al., "A Conformation- and Ion-Sensitive Plasmonic Biosensor," Nano Lett., 11, (3), 1098-1105 (2011)). While monitoring the peak shift is currently the most common method of detecting analyte binding, it has been shown that it is the increase in the scattered intensity over such a large portion of the resonance spectrum that allows for the fractional occupancy of the array to be determined spectroscopically, while simultaneously enabling LSPR imaging via the CCD camera. (M. P. Raphael et al., "A New Methodology for Quantitative LSPR Biosensing and Imaging," Anal. Chem., 84(3), 1367-73 (2012)).

Figure 1C:
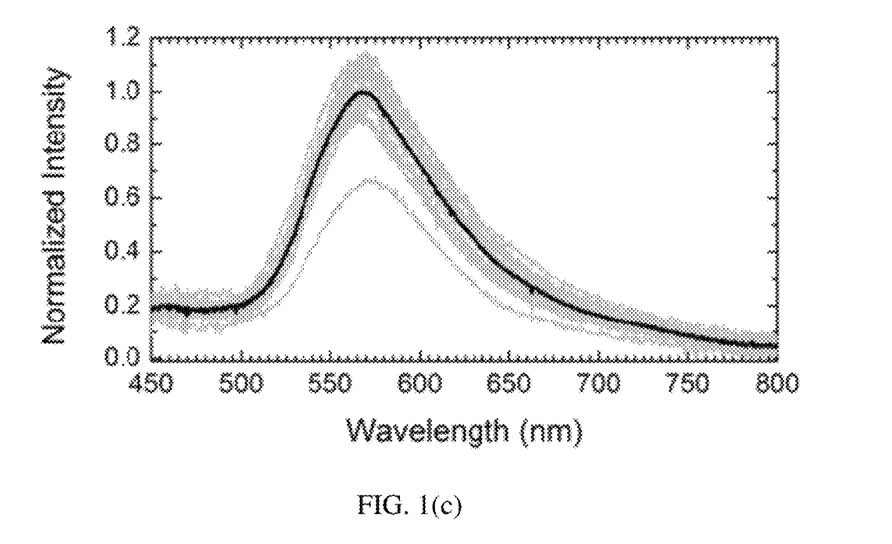
FIG. 1(c) shows normalized spectra from 18 individual nanostructures taken in air. Individual spectra are superposed (gray curves) and compared to the ensemble average (black curve).

The calibration of hundreds of nanostructures in batch mode requires that the spectral properties of individual nanostructures closely resemble that of the array ensemble average. Topological studies of the nanostructures by AFM revealed small variations in nanostructure shape due to the fabrication process (FIG. 1(a) inset). To investigate the corresponding spectral variations amongst individual nanostructures, single-nanostructure spectroscopy using dark-field microspectroscopy was conducted in air on a witness row of 18 nanostructures fabricated on the same chip as the array used for biosensing. The results, summarized in FIG. 1(c), show that while small variabilities in the shape, amplitude, and resonant wavelength could be discerned, the spectrum of nearly every nanostructure fell close to the ensemble average. In the CCD imagery, these distributions can be manifested as a distribution of intensities, as shown in the FIG. 2 insets, which have been contrast enhanced to highlight the intensity variations.

Figure 2:
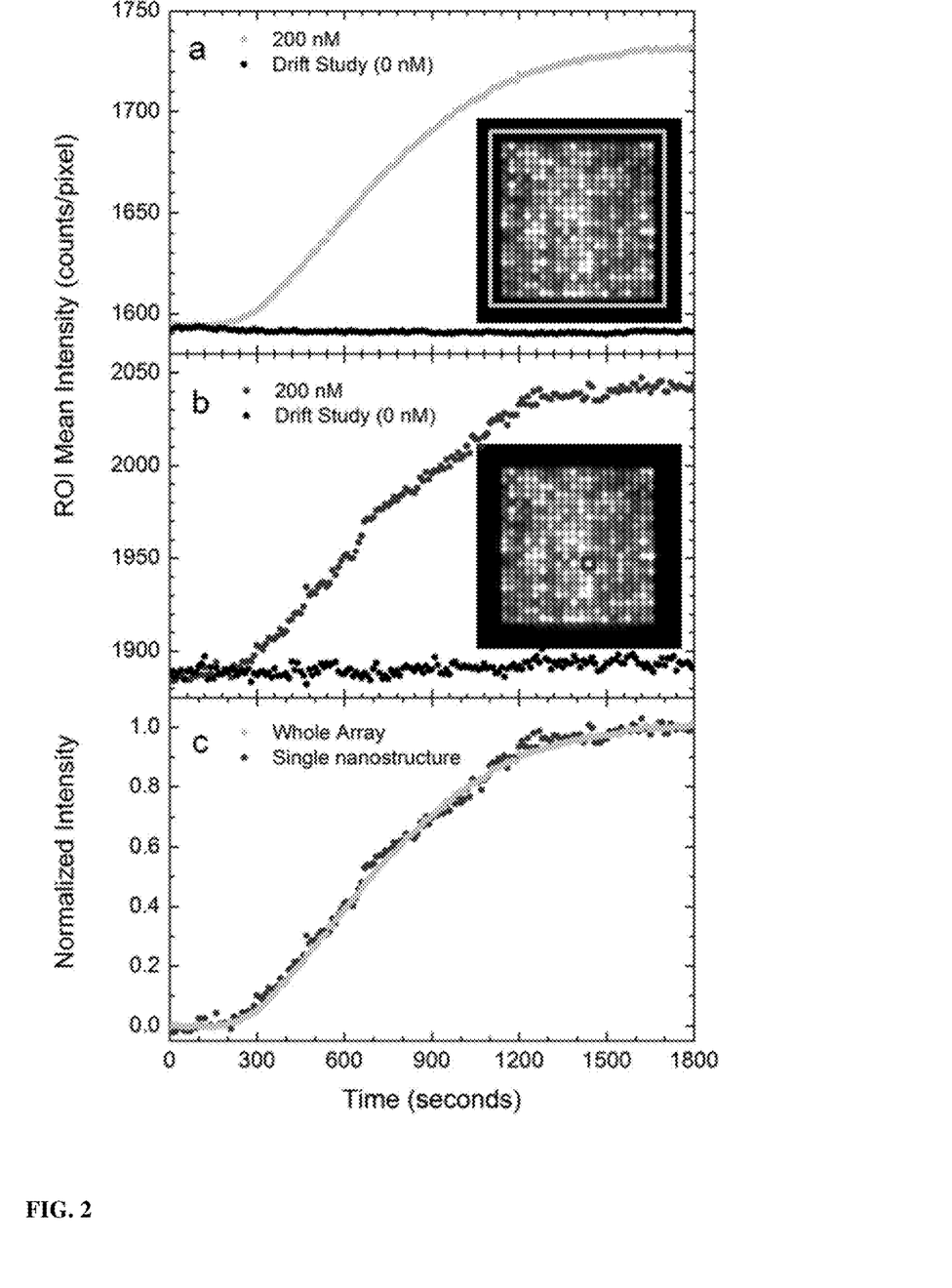
FIG. 2 shows LSPR imaging time-course measurement from a 200 nM anti-c-myc specific binding study.

FIG. 2 details the time course of a 200 nM anti-c-myc specific binding study as measured by LSPR imagery and demonstrates a straightforward image analysis technique for qualitatively monitoring the kinetics down to the single nanostructure. FIG. 2(a) shows the enhanced counts from binding for the entire array (84×84 pixels) as calculated from the mean intensity of the pixels bounded within the light gray region of interest (ROI) square:

$$I(r_i, t_n) = \frac{1}{m_i} \sum_{\vec{x} \in r_i} I_{image}(\vec{x}, t_n) \tag{1}$$

where $m_i$ is the number of pixels in the ROI denoted as $r_i$ and $t_n$ is the time point. Also shown is a drift study that preceded the introduction of analyte (black squares) in which SFM flowed over the array for 30 minutes at 10 µL/min. In contrast to simple buffers, SFM typically contains anywhere from 50 mg/L to 1000 mg/L of additional proteins such as albumin, transferrin and insulin, which can potentially biofoul the sensors. Despite this presence, the measurements demonstrated minimal drift, and sensitivity to analyte was retained. Additional studies demonstrating minimal non-specific binding studies between the antibody and the SAM-functionalized surface were conducted using a Bio-Rad XPR36 surface plasmon resonance instrument.

FIG. 2(b) plots the same two experiments but with the ROI now comprising only a single nanostructure, as selected by a 4×4 pixel (410×410 nm) square ROI shown in black near the center of the array. The relative response of the nanostructure is compared directly to that of the entire array in FIG. 2(c) by plotting the normalized counts: $[I(r_i,t_n)-I(r_i,t_o)]/[I(r_i,t_f)-I(r_i,t_o)]$ where $I(r_i,t_o)$ is the average of the first twenty time points and $I(r_i,t_f)$ is the average of the last twenty time points. This same straightforward ROI approach can be applied to any nanostructure in the array, giving four hundred independent and label-free nanosensors within the 8 µm×8 µm area.

FIG. 2(c) highlights that the response within the nanoscale ROIs are typically in excellent agreement with that of the entire array. Thus, if the entire array can be calibrated for the determination of the fractional occupancy, f(t), this homogeneous response in principle can be utilized to simultaneously calibrate the individual nanostructures. This at first can seem surprising given the likelihood that the surface-bound receptors on any given nanostructure will have an inhomogeneous spatial distribution and response to analyte. (K. M. Mayer et al., "A single molecule immunoassay by localized surface plasmon resonance," *Nanotechnology*, 21, (25) (2010) and G. J. Nusz et al., "Label-free plasmonic detection of biomolecular binding by a single gold nanorod," *Anal. Chem.*, 80, (4), 984-989 (2008)). It is reasonable, however, given that both the theory of random sequence adsorption (E. L. Hinrichsen et al., "Geometry of random sequential adsorption," *J. Stat. Phys.*, 44, (5-6), 793-827 (1986)) and experimental estimates using similarly functionalized gold surfaces (S. Chen et al., "Plasmon-Enhanced Colorimetric ELISA with Single Molecule Sensitivity," *Nano Lett.*, 11, (4), 1826-1830 (2011) and L. S. Jung et al., "Binding and dissociation kinetics of wild-type and mutant streptavidins on mixed biotin-containing alkylthiolate monolayers," *Langmuir*, 16, (24), 9421-9432) (2000)) are in agreement that nanostructures of this size can accommodate hundreds of proteins, thus averaging out the effect of such inhomogeneities. Next is the discussion on how this qualitative observation can be expanded into a data analysis formalism that allows for the quantitative determination of the fractional occupancy within the imagery.

Quantitative Biosensing with Single Nanostructures

We have previously reported a methodology that allows for the determination of the fractional occupancy of the entire array from the spectral data, denoted here as $f_s(t)$. (M. P. Raphael et al., "A New Methodology for Quantitative LSPR Biosensing and Imaging," *Anal. Chem.*, 84(3), 1367-73 (2012)). In short, the number of counts at wavelength, λ, accumulated by the spectrometer during time interval $t_n$ can be written as a linear response model with Poisson counting noise, $\eta_{Poisson}$, in terms of the $f_s$ for a specifically-bound monolayer perturbing the localized surface plasmon resonance:

$$N_\lambda(t_n)=g(t_n)\cdot[a_\lambda f_S(t_n)+b_\lambda]+\eta_{Poisson} \quad (2)$$

The model parameters $a_\lambda$ and $b_\lambda$ represent the wavelength-dependent dielectric response caused by the bound analyte and the initial background of the LSPR array, respectively. The overall time-dependent coefficient, $g(t_n)$, is initially set to one at the beginning of the experiment but can account for drift and jump processes that cause variations in the scattered light intensity with no wavelength dependence. Generally, $g(t_n) \approx 1$ and can be ignored in most situations. For a given nanostructure array and experimental conditions the $b_\lambda$ is determined when no analyte is present at the beginning of the experiment and the $a_\lambda$ is determined by the injection of a saturating injection of known concentration at the end of the experiment. The time-dependent functions $g(t_n)$ and $f_S(t_n)$ can be determined by non-linear regression within a Poisson noise model for the counts at each time interval, $t_n$.

To assess whether the imagery of single nanostructures can capture the fractional occupancy information found in whole-array spectroscopy, a simple generative model is proposed for how the image data is formed, similar to that used in analyzing the spectroscopy data:

$$I(r_i,t_n)=A(r_i)\cdot f_I(r_i,t_n)+B(r_i)+\eta_{Poisson} \quad (3)$$

Here the model parameters $a_\lambda$ and $b_\lambda$ are analogously represented by the spatially dependent parameters $A(r_i)$ and $B(r_i)$ for the determination of the fractional occupancy from the image data, $f_I(r_i,t_n)$. Since the size of the array is small compared to the diffusion length of the analyte over the exposure time of the CCD camera, the concentration is effectively uniform. This allows $A(r_i)$ and $B(r_i)$ to be determined via multi-variate linear regression by setting $f_I(r_i,t_n)=f_S(t_n)$, thus, calibrating the entire array via imagery. Once the array is calibrated, inhomogeneous fractional occupancy can be estimated as:

$$\hat{f}_I(r_i, t_n) = \frac{I(r_i, t_n) - B(r_i)}{A(r_i)} \quad (4)$$

In order to determine if this relatively simple treatment of the imagery data is effective, the variance in the local response, $\hat{f}_I(r_i,t_n)$, of the nanostructure array from $f_S(t_n)$ over the ROIs can be calculated:

$$\sigma^2(r_i) = \frac{1}{N}\sum_{n=1}^{N} |\hat{f}_I(r_i, t_n) - f_S(t_n)|^2 \quad (5)$$

The resulting image map will show what parts of the array are capable of being calibrated for the determination of the local fractional occupancy.

As an example of the applicability of this approach to molecular and cell biology, the determination of fractional occupancy versus time at the nanoscale to the secreted antibodies contained within the supernatant of cultured MYC1-9E10.2 hybridoma cells was demonstrated. The harvested antibodies experiment was conducted by simply centrifuging the cells at 3000 rpm for 5 minutes, collecting the supernatant and applying that solution to the nanostructures via the microfluidic setup at a flow rate of 10 μL/min. The concentration of secreted anti-c-myc antibodies in the supernatant was independently determined by ELISA to be 9 nM. The nanostructure calibration was conducted as described above by introducing a known concentration of commercial anti-c-myc (250 nM) over the nanostructures immediately following the harvested antibody experiment.

Figure 3:
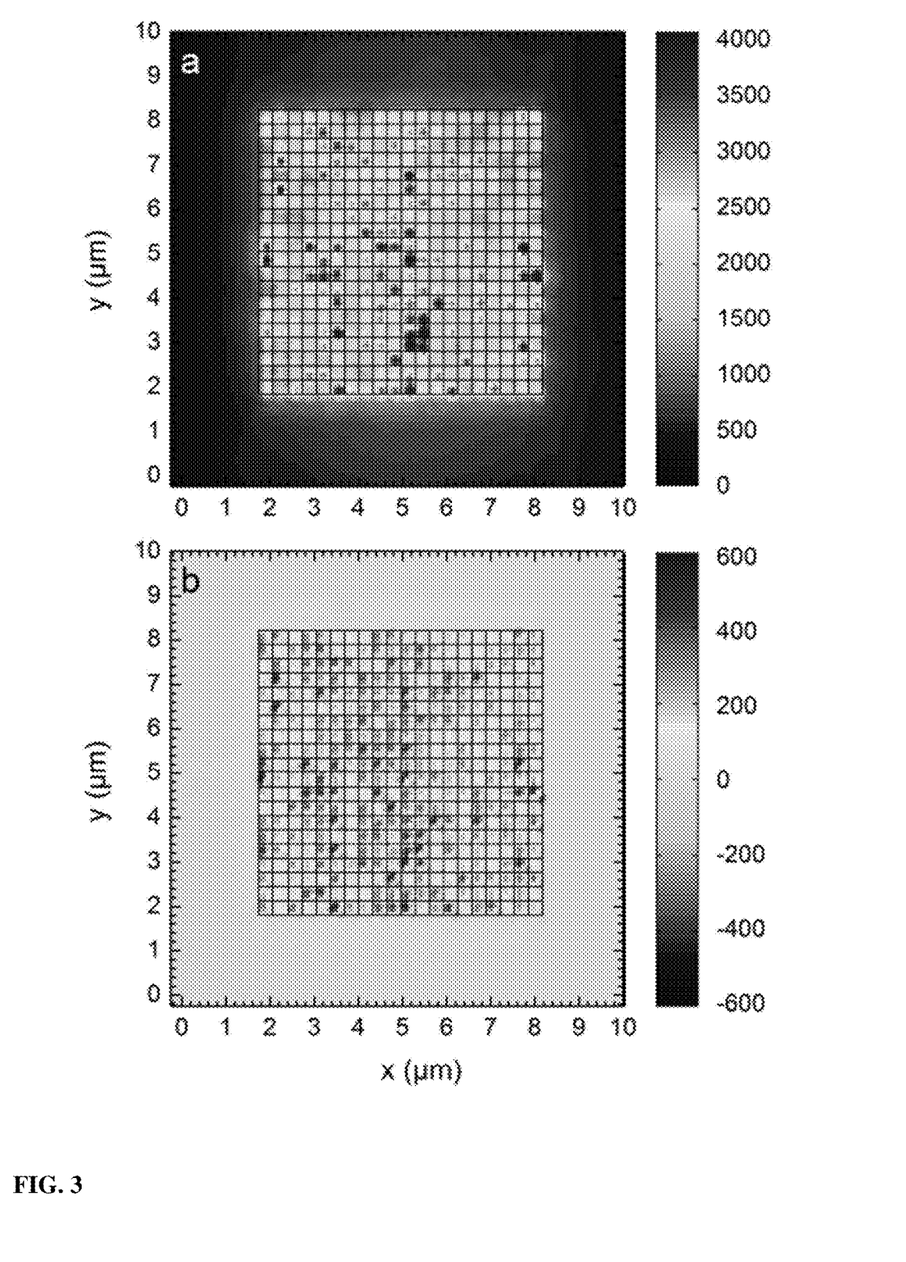
FIG. 3(a) shows a background response map, $B(r_i)$
FIG. 3(b) shows a linear response map, $A(r_i)$, of the array for the anti-c-myc harvested antibody study, calculated for every pixel in the image (ROI: 1×1 pixel). The calibration was conducted immediately following the harvested antibody study by injecting 250 nM of commercial anti-c-myc in serum-free medium. A grid of 4×4 pixel squares has been superimposed to demarcate the location of the nanostructures in the imagery.

FIG. 3 displays the $B(r_i)$ and $A(r_i)$ response maps of a 12.4×12.4 μm area centered about the array for every pixel in the image (ROI: 1×1 pixel). A grid of 4×4 pixel (410×410 nm) squares has been superimposed over each map to demarcate the location of each nanostructure from the imagery. In FIG. 3(a), the dark regions of the coefficient map for the background term, $B(r_i)$, are highly correlated with the brightest nanostructures in the CCD image (FIG. 2 inset), as is to be expected for the background contribution to the fit. The coefficient map for the linear response term, $A(r_i)$, is shown in FIG. 3(b). Again the strongest positive responses are located within the squares of the grid and thus are correlated with the locations of the nanostructures. The optimization was repeated using a sliding ROI window of the same size as the grid (4×4 pixels) which had the advantage of closely approximating the size of the diffraction-limited image of the nanostructures. In addition, this larger ROI averaged out the presence of a slight drift of ~2 pixels (1.7 nm/min) which occurred over the course of the 2 hour run.

Figure 4:
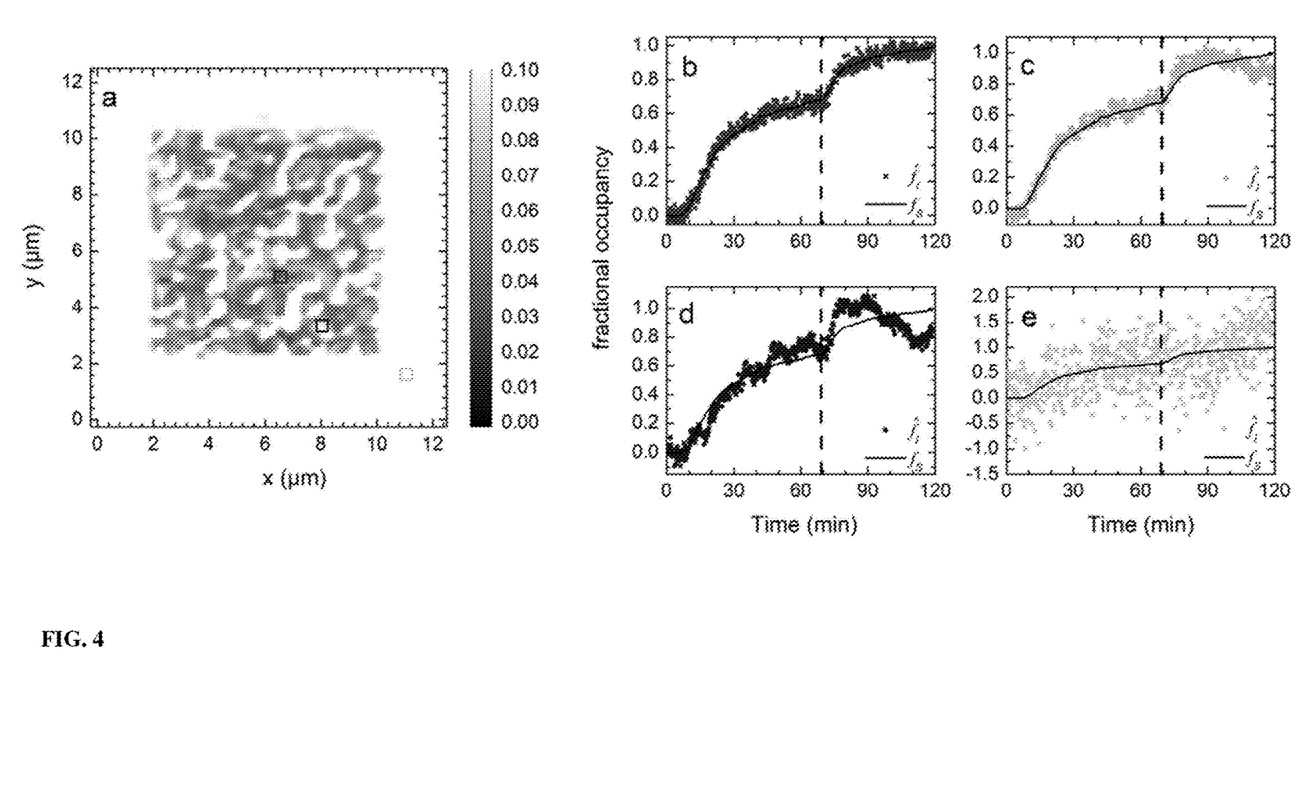

The results of the 4×4 pixel sliding ROI calibration and analysis are summarized in FIG. 4. FIG. 4(a) shows the error estimate map of which presents the deviations between $f_I$ and $f_S$ as a grey-scale map. The shape of the array is clearly reproduced on the map due to the fact that it is only within the array area that $f_I$ and $f_S$ are within reasonable agreement. In fact, by setting the scale of $\sigma_i$ on the map to be between 0 and 0.1 we show that over 75% of the area encompassed by the array can be well calibrated with the spectroscopically determined fractional occupancy. To illustrate the deviations between $f_I$ and $f_S$ associated with a given the data from specific ROIs are plotted in FIGS. 4(b)-(e) with $\sigma_i$=0.03, $\sigma_i$=0.05, $\sigma_i$=0.10, and $\sigma_i$=0.42, respectively. The color of the ROI data points are matched with that of the ROI square label on the response map and the vertical dashed line indicates the end of the harvested anti-c-myc antibody run, at which point 250 nM of commercial anti-c-myc was injected. There is excellent agreement between the two for $\sigma_i \leq 0.05$, which deteriorates somewhat at $\sigma_i$=0.1, while there is no statistically meaningful correlations for the ROI located outside of the array.

The results in FIG. 4 demonstrate that for the majority (over 75%) of the array, $f_I$ can be determined to within 10% of $f_S$ using ROIs of a similar size to that of the diffraction limited image of each nanostructure. Even with the reproducibility of fabricating by EBL, however, it was not possible to calibrate the entire array area to within this range of error. This is not an impediment though since a great advantage to this approach is that those ROIs which do not calibrate to within a set specification can simply be ignored while those that do can be used for the quantitative analysis. As such, this LSPR imaging technique allows for label-free and quantitative characterization of cell supernatant with minimal preparation and nanomolar sensitivity, utilizing hundreds of nanostructures independently calibrated to within the user's specification. In its current form, this technology sets the stage for future applications in high density proteomics arrays as well as for imaging analyte concentration gradients in complex live cell environments.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A method for calibrating multiple nanostructures in parallel for quantitative biosensing, comprising:
   fabricating at least one array of functionalized plasmonic nanostructures for localized surface plasmon resonance (LSPR) biosensing and imaging on a glass coverslip compatible for use in a standard microscope using electron beam nanolithography;
   simultaneously measuring CCD-based LSPR imagery data of each individual nanostructure and LSPR spectral data of the array;
   analyzing the LSPR spectral data of the array to determine the fractional occupancy of the entire array;
   analyzing the imagery data to determine the fractional occupancy of individual nanostructures;
   creating an image map to show a deviation between the fractional occupancy of the entire array and the fractional occupancy of individual nanostructures; and
   calibrating for quantitative biosensing only individual nanostructures within a defined deviation while ignoring nanostructures outside of the defined deviation.

2. The method of claim 1, wherein the functionalized plasmonic nanostructures comprise functionalized gold plasmonic nanostructures.

3. The method of claim 1, wherein the pitch between the arrays is in the range from 150 to 1000 nm.

4. The method of claim 1, wherein the size of the patterned nanostructures is in the range from 50 to 150 nm.

5. The method of claim 1, wherein the shape of the nanostructures comprises rectangles, squares, discs, ovals, or any combination thereof.

6. The method of claim 1, wherein the nanostructure arrays can be regenerated.

7. The method of claim 6, wherein the nanostructure arrays are regenerated by plasma ashing.

* * * * *